United States Patent [19]

Barratt et al.

[11] Patent Number: 4,612,331

[45] Date of Patent: * Sep. 16, 1986

[54] SKIN TREATMENT COMPOSITION

[75] Inventors: Martin D. Barratt, Sharnbrook; Paul A. Bowser, Wirral; James A. Durrant, Bebington; Dieno George; Keith J. Hall, both of Wirral; John C. Hill, South Wirral; Michael R. Lowry, Chester; Colin Prottey, Wirral, all of England

[73] Assignee: Lever Brothers Company, New York, N.Y.

[*] Notice: The portion of the term of this patent subsequent to Mar. 26, 2002 has been disclaimed.

[21] Appl. No.: 688,948

[22] Filed: Jan. 4, 1985

Related U.S. Application Data

[63] Continuation of Ser. No. 462,641, Jan. 31, 1983, Pat. No. 4,507,319.

[30] Foreign Application Priority Data

Feb. 2, 1982 [GB] United Kingdom ............... 8202886
Jul. 20, 1982 [GB] United Kingdom ............... 8220981

[51] Int. Cl.⁴ ............................................. A61K 31/20
[52] U.S. Cl. .................................................. 514/558
[58] Field of Search ......................................... 514/558

[56] References Cited

U.S. PATENT DOCUMENTS

| | | | |
|---|---|---|---|
| 3,806,593 | 4/1974 | Swanbeck et al. | 424/28 |
| 3,988,470 | 10/1976 | Van Scott et al. | 424/283 |
| 4,105,782 | 8/1978 | Yu et al. | 424/283 |
| 4,197,316 | 4/1980 | Yu et al. | 424/317 |
| 4,234,599 | 11/1980 | Van Scott et al. | 424/279 |
| 4,507,319 | 3/1985 | Barratt et al. | 514/546 |

FOREIGN PATENT DOCUMENTS 7785 4/1982 European Pat. Off. .
1561475 2/1980 United Kingdom .

Primary Examiner—Leonard Schenkman
Attorney, Agent, or Firm—Milton L. Honig; James J. Farrell

[57] ABSTRACT

A cosmetically acceptable composition for topical application to human skin comprises from 0.1 to 20% by weight of a substituted 2-hydroxyoctanoic acid or 2-ketooctanoic acid or a mixture thereof, together with an amount of a special neutralizing agent sufficient to adjust the pH of the composition to a value of from 3 to 7. The special neutralizing agent is one having a cation whose ionic radius is at least 100 pm.

1 Claim, No Drawings

SKIN TREATMENT COMPOSITION

This is a continuation application of Ser. No. 462,641, filed Jan. 31, 1983, now U.S. Pat. No. 4,507,319.

The invention relates to cosmetically acceptable compositions for application to the skin, particularly for the prevention or treatment of acne or of other skin disorders, and for generally improving the condition of the skin.

A soft, supple and flexible skin has a marked cosmetic appeal and is an attribute of normal functioning epidermis. The outer layer of the epidermis, that is the stratum corneum, can however become dry and flaky following exposure to adverse climatic conditions, or excessive contact with detergents or solvents which result in the loss of skin moisture, with the result that the skin loses its soft, supple and flexible characteristics. Emollients such as fats, phospholipids and sterols have in the past been used to soften dry skin, but it is apparent that these emollients are only partially effective as a remedy for this type of condition.

Also, topical application to the skin of classical humectants is unlikely to alleviate this problem since they are not particularly skin substantive and are generally rinsed from the skin during washing.

So far as acne is concerned, the primary symptom is a disorder in the keratinisation of the upper part of the pilosebacous follicle. The follicular ostium becomes obstructed by hyperkeratinised and cohesive horny cells to form a microcomedone. Due to the accumulation of these hyperkeratinised cells, the follicle develops into a microcyst which may evolve as an inflammatory lesion known as a papule, or a non-inflammatory lesion known as an open comedone. The external orifice of the follicle is not visible in the microcyst, but in the open comedone, it becomes distended by a mass of darkly pigmented horny cells.

As acne develops, the follicular epithelium may break-up and cause an eruption into the dermis of keratin and sebum. The sebum contains free fatty acids derived primarily from the lytic effect of bacterial lipases (especially from *Propionibacterium acnes*) on sebum triglycerides. Inflammation due to the released free fatty acids and other bacterial by-products can ensue and a lymphocyte reaction may transform the microcyst into a papule and then into a pustule with the gathering of pus.

It is accordingly apparent that any treatment directed to inhibiting the release of these bacterial by-products of which free fatty acids from sebum triglycerides are an example, so arresting hyperkeratinisation of the follicular ostium, would effect a regression of the primary symptoms of acne and would limit the development of new acneic lesions, particularly non-inflammatory lesions (comedones).

Attempts have in the past been made to inhibit the release of these bacterial by-products by removal of the microorganisms, such as *P. acnes*, that are believed to be implicated, but these attempts have only met with limited success. The use, for example, of antibiotics can be effective in this respect, but the over liberal use of such pharmaceuticals is not to be condoned in view of their effect on gut flora and the development of antibiotic resistant strains of pathogenic organisms.

The topical application to acneic comedones of skin-tolerable organic acids, such as lactic acid, has also met with limited success in view of the inability of such acids to maintain a skin pH low enough to inhibit the proliferation of skin microflora for a sufficient length of time to effect regression of the disease.

Other prior proposals include those of van Scott & Yu in U.S. Pat. No. 3,988,470 which describes the treatment of acne with hydroxy alkanoic acids having up to 6 carbon atoms in the molecule. Also, Yu & van Scott in U.S. Pat. No. 4,197,316 describe products for the treatment of dry skin which include hydroxy alkanoic acids having up to 6 carbon atoms in the molecule, such acids being buffered with triethanolamine. Also, Unilever EPA No. 7785 discloses skin treatment compositions containing 2-hydroxyoctanoic acid in which the pH is adjusted to values of less than 7 by addition of sodium hydroxide.

We have now discovered that the topical application to acneic skin of 2-hydroxyoctanoic acid, together with a neutralising agent other than sodium hydroxide which is used to increase slightly the pH value of the composition, surprisingly holds the pH at the skin surface at a low value for a relatively long time without the development of skin irritation such that the inhibitory effect on skin microflora is much greater than that following the topical application of other organic acids of differing chain length. We have also discovered that the corresponding keto acid, 2-ketooctanoic acid, is similarly effective. The consequence of this is that the subsequent appearance at the skin surface of free fatty acids is also reduced, inflammation diminishes and the acneic condition recedes.

We have also discovered that topical application of these substituted octanoic acids in an acid-buffered composition surprisingly enhances the extensibility of stratum corneum, such that skin, especially dry, flaky or otherwise damaged skin can be made more soft, supple and flexible.

The invention accordingly provides a cosmetically acceptable aqueous composition for topical application to human skin, which composition comprises:

(i) from 0.1 to 20% by weight of a substituted octanoic acid chosen from 2-hydroxyoctanoic acid, 2-ketooctanoic acid or a mixture thereof; and (ii) an amount of a neutralising agent sufficient to adjust the pH of the composition to a value of from 3 to 7, the neutralising agent having a cation whose ionic radius is at least 100 pm.

The composition comprises a substituted octanoic acid chosen from 2-hydroxyoctanoic acid, 2-ketooctanoic acid or a mixture of these acids, or a precursor of either acid which is capable of releasing the substituted octanoic acid on the skin after topical application of the composition. Careful screening of related acids has shown that the effectiveness of the composition in the treatment of acne depends specifically on the presence of 2-hydroxyoctanoic acid and/or 2-ketooctanoic acid, due to their ability to maintain the skin at a low pH for a time sufficient to reduce skin microflora associated with acne. The corresponding unsubstituted octanoic acids are virtually ineffective in this respect. Comparison with hydroxy acids and keto acids of shorter chain length than the substituted octanoic acid has also revealed that it is only these specific acids which are particularly effective in the treatment of acne. Evidence to support this position with data derived from comparative experiments will be given later in this specification. Comparison with hydroxy and keto acids of longer chain length than the substituted octanoic acids was not carried out in view of skin irritation generated by use of these longer chained acids, which may render them unsuitable for topical use.

It has also been shown by screening of related acids that it is only 2-hydroxyoctanoic acid and 2-ketooctanoic acid which possess the ability, when buffered to a suitable acid pH value, of increasing the extensibility of stratum corneum to a surprising extent.

Evidence to support this surprising result is also given later in the specification.

The amount of the substituted octanoic acid to be employed in the composition of the invention is from 0.1 to 20%, preferably from 1 to 10%, most preferably from 1 to 5% by weight of the composition.

It has been shown that if the composition contains less than 0.1% by weight of the substituted octanoic acid, then it is unlikely to be effective in the general improvement of skin condition or in the treatment of acne, as the pH of the skin following topical application of the composition will either not reach the desired value, or will not be maintained at the desired value for a long enough period of time to be effective in inhibiting skin microflora. On the other hand, if the composition contains more than 20% by weight of the substituted octanoic acid, it is unlikely that the effectiveness of the composition in generally improving the condition of the skin, and specifically in the treatment of acne will be increased beyond that benefit derived from the use of either acid at the 20% by weight level. It is also possible that use of an excessive amount of the substituted acid might result in skin irritation.

The composition according to the invention will also contain a neutralising agent in an amount sufficient to adjust the pH of the composition to a value of from 3 to 7.

It is important that the adjustment of pH to a value within this range is carried out with a neutralising agent that maintains the substituted octanoic acid in the monomeric form, without precipitation of the corresponding substituted octanoate since it is apparent that it is this form of the acid which has the greatest influence on plasticisation of the skin.

The neutralising agent should therefore be one having a cation whose ionic radius is at least 100 pm, since it has been found that those whose cations have ionic radii of less than 100 pm can yield a substituted octanoic acid salt which has little or no skin benefit.

Preferably the neutralising agent is one whose cation has an ionic radius of at least 130 pm, most preferably at least 150 pm and ideally greater than 200 pm. Whereas it is apparent the greater the ionic radius of the cation the more suitable is the neutralising agent for use in the composition of the invention, providing of course that the neutralising agent is cosmetically acceptable, it can be stated that the ionic radius of the cation should not normally exceed 10,000 pm, as the ability of the agent to behave as a neutralising agent in the adjustment of pH will be diminished at such high values.

Examples of suitable neutralising agents are potassium hydroxide (ionic radius of $K^+$ is 133 pm) and ammonium hydroxide (ionic radius of $NH_4^+$ is 142 pm).

The preferred neutralising agent is however an amine, especially an alkanolamine, such as a mono-, di- or tri-alkanolamine, or a mixture thereof. The most preferred alkanolamines are a propanolamine, ideally diisopropanolamine, and an ethanolamine, ideally triethanolamine. It is to be noted that the precise ionic radii of the cations of all amines are difficult to measure, but it is clear that they will exceed the 142 pm which is the radius of the ammonium cation ($NH_4^+$) from which amines are derived.

The choice of a neutralising agent having a cation whose ionic radius is at least 100 pm to adjust the pH of the composition to a value within the range of from 3 to 7 is important, as it is thereby possible effectively to increase the pH of the composition from a value of about pH 2 to a value within the desired range, without causing the substituted octanoic acid to precipitate out. It has accordingly been found that if pH adjustment is attempted with sodium hydroxide, the ionic radius of the cation $Na^+$ being 95 pm, then precipitation of the sodium salt of the substituted octanoic acid (i.e. as sodium 2-hydroxyoctanoate or as sodium 2-ketooctanoate) can occur which can impede pH adjustment of the skin to such an extent that the inhibitory effect on skin microflora is minimal and that the acneic condition does not regress. Furthermore, enhancement of stratum corneum extensibility also may not be realised.

Similarly, adjustment of pH using, for example, calcium hydroxide ($Ca^{++}$:99 pm), lithium hydroxide ($Li^+$:60 pm) and magnesium hydroxide ($Mg^{++}$:65 pm) is to be avoided because in each case the ionic radius of the cation is less than 100 pm and precipitation of the corresponding substituted octanoate can occur.

The pH of the composition should be from 3 to 7, preferably from pH 3 to 5, most preferably from pH 3.8 to 4.5. Tests have shown that the application to the skin of a composition having a pH value of less than pH 3 is more likely to cause skin irritation than one having a pH value at or above this figure. Also, the application to the skin of a composition having a pH value of greater than 7 can have little inhibitory effect on skin microflora, with the consequence that the acneic condition does not regress. Evidence to demonstrate how important is the adjustment of the pH of the composition, particularly to a value within the preferred range, will be given later in this specification.

The composition according to the invention also comprises water to provide a solvent for the substituted octanoic acid. Usually, the composition will contain from 5 to 95%, preferably 10 to 80% by weight of water based on the total composition. Compositions containing less than 5% by weight of water when applied to the skin are likely to leave it in a particularly dehydrated condition, and also may not be suitable for maintaining the substituted octanoic acid in solution. On the other hand, compositions which contain more than 95% by weight of water are likely to prove too wet for practical application to the skin, although they will still be operable for their intended use.

It has also been discovered that a mixture of the substituted octanoic acid and a $C_2$ to $C_4$ alkyl lactate, when applied topically to human skin, is capable of reducing the total viable count of aerobic and anaerobic bacteria to a surprising extent. Evidence to support this finding will also be given later in this specification.

The composition according to the invention can therefore also optionally comprise a $C_2$ to $C_4$ alkyl lactate or a mixture of such lactates. Examples of alkyl lactates are ethyl lactate, n-propyl lactate, iso-propyl lactate, n-butyl lactate, iso-butyl lactate and t-butyl lactate. The preferred lactate is ethyl lactate.

The advantage of employing such alkyl lactates, particularly in the treatment of acne, is thought to be due to their ability to pass through the epidermis to reach intact the sebum in the sebaceous gland of the pilosebaceous follicle, and there to dissolve in the sebum lipids included short chain alkanols, diols, short chain fatty acids, urea and salting in electrolytes such as sodium iodide, sodium thiocyanate and potassium hydroxide. By contrast, other compounds which reduce the critical micelle concentration of nonionic surfactants, such as long chain alcohols, for example butanol and amyl alcohol; polyols, for example sorbitol and salting out electrolytes, for example sodium sulphate, sodium carbonate and sodium hydroxide, do not enhance the increase in skin plasticisation attributable to the substituted octanoic acid.

A plasticisation potentiator is accordingly defined as a compound which is capable, at a concentration of 5% by weight of increasing the cloud point temperature of a 0.025 M aqueous solution of polyoxyethylene(8-)nonylphenyl ether by at least 2° C. Preferably the plasticisation potentiator is one which is capable of increasing the cloud point temperature by at least 10° C., most preferably by at least 13° C.

It should be explained that the "cloud point" is a measure of the inverse solubility of a nonionic surfactant with temperature and can be determined by heating a standard clear aqueous solution of the nonionic surfactant until the solution becomes visibly cloudy and then measuring the temperature at which the solution becomes clear again as it cools.

The cloud point temperature can conveniently be determined automatically using the equipment and method described by Baum et al in Mat. Res. Std. 4 26 (1964).

Examples of suitable compounds functioning as plasticisation potentiators, together with the respective elevated cloud point temperature obtained in each case when using the standard test defined hereinbefore are listed below in Table 1.

TABLE 1

Elevation of the cloud point temperature of a 0.025 M aqueous solution of polyoxyethylene(8)nonylphenyl ether in the presence of plasticisation potentiators

| Plasticisation potentiator (5% by weight) | 0.025 M aqueous solution of polyoxyethylene(8)nonyl phenyl ether | |
|---|---|---|
| | Cloud point temperature (°C.) | Elevation of cloud point temperature (°C.) |
| None (control) | 44 | 0 |
| Methanol | 55 | 11 |
| Ethanol | 58 | 14 |
| Propanol | 57 | 13 |
| Propane-1,2-diol | 52.6 | 8.6 |
| Butane-1,4-diol | 57.2 | 13.2 |
| Diethane-1,2-diol | 47 | 3 |
| Dipropane-1,2-diol | 58 | 14 |

Other examples of plasticisation potentiators are n-methylpyrrolidone, 2-pyrrolidone, butan-1,3-diol, pentan-2,4-diol, and hexan-2,5-diol.

By way of comparison, we list below in Table 2 examples of organic compounds which do not satisfy the cloud point test in that the increase in cloud point temperature is less than 7° C.; in some cases a reduction of cloud point temperature is observed.

TABLE 2

Elevation (or reduction) of the cloud point temperature of a 0.025 M aqueous solution of polyoxyethylene(8)nonylphenyl ether in the presence of compounds which are not plasticisation potentiators

| Compound which is not a plasticisation potentiator (5% by weight) | 0.025 M aqueous solution of polyoxyethylene(8)nonyl phenyl ether | |
|---|---|---|
| | Cloud point temperature (°C.) | Elevation of cloud point temperature (°C.) |
| None (control) | 44 | 0 |
| Ethane-1,2-diol | 43.2 | −0.8 |
| Glycerol | 42.9 | −1.1 |
| Butanol | 24 | −20 |

The plasticisation potentiator that can optionally be employed in compositions of the invention should form from 0.1 to 20%, preferably from 0.5 to 10% by weight of the composition.

It is apparent that if the composition contains a plasticisation potentiator at a concentration of less than 0.1% by weight, then it is unlikely to contribute significantly to the increase in the extensibility of stratum corneum attributable to the substituted octanoic acid, whereas, if the composition contains more than 20% by weight of a plasticisation potentiator, then it is unlikely that the plasticisation of the skin will be further increased beyond that obtainable when 20% by weight of the plasicisation potentiator is employed.

The invention also provides a process for preparing an aqueous composition for topical application to the skin, particularly for use in treating acne, which comprises the steps of:

(i) dispersing in water a substituted octanoic acid chosen from 2-hydroxyoctanoic acid, 2-ketooctanoic acid or a mixture thereof;

(ii) adjusting the pH of the dispersion to a value of from 3 to 5 with a neutralising agent as herein defined to provide a composition comprising from 0.1 to 20% by weight of the substituted octanoic acid; and (iii) subsequently packaging the composition in a container.

The invention also furthermore provides a method for alleviating the symptoms of acne which comprises the step of applying topically to acneic skin an effective amount of an aqueous composition comprising a substituted octanoic acid chosen from 2-hydroxyoctanoic acid and 2-ketooctanoic acid, optionally together with a $C_2$ to $C_4$ alkyl lactate and a $C_3$ to $C_6$ 2-hydroxyalkanoic acid or a $C_3$ to $C_6$ 2-ketoalkanoic acid, the pH of the composition being adjusted to a value of from pH 3 to 5 by the addition of a neutralising agent without precipitation of the substituted octanoic acid.

The invention also provides for the use of 2-hydroxyoctanoic acid or 2-ketooctanoic acid in the treatment of acne.

The composition according to the invention can be formulated as a liquid, for example, as a lotion or milk, which can be applied directly to the skin, preferably by means of a pad, or a swab, tissue or towel, impregnated with the composition. Alternatively, a mechanical applicator such as a roll-ball dispensing device or an aerosol spray can be employed. Alternatively, the composition of the invention can be semi-solid, for example as a cream or gel which is used in conjunction with a suitable applicator such as a stick dispenser, or simply a bottle, tube or lidded jar.

where hydrolysis by lipases of bacterial origin will yield lactic acid and the corresponding alcohol. The alcohol so formed is thought to exhibit antibacterial activity when formed in situ in the sebaceous glands and in this way the bacterial population, whose lipase activity otherwise contributes to acne formation following hydrolysis of sebum triglycerides, thus releasing free fatty acids, can thereby be reduced. Also, the lactic acid which is formed in situ is capable of reducing the pH of the environment to a value below pH 6 which will inhibit bacterial lipase activity. Free lactic acid also appears to reduce keratinisation. The net result is that release from the sebum lipids of free fatty acids, which contribute to the development of acne, is reduced, and remission of the acne condition can be observed.

The amount of $C_2$–$C_4$ alkyl lactate that can be employed in the composition of the invention is from 0.1% to 50%, preferably from 1 to 25% by weight of the composition.

It is apparent that if the composition contains less than 0.1% by weight of the alkyl lactate, then the additional benefit of including the lactate in the composition is unlikely to be realised, whereas if the composition contains more than 50% by weight of the alkyl lactate, it is unlikely that the effectiveness of the composition in the treatment of acne will be increased beyond that derived from the use of the lactate at the 50% by weight level.

It has also been discovered that a mixture of the substituted octanoic acid and a 2-hydroxyalkanoic acid of shorter carbon chain length and/or a 2-ketoalkanoic acid of shorter carbon chain length, when applied topically to human skin, is capable of enhancing still further the increase in extensibility of stratum corneum attributable to the substituted octanoic acid itself.

The composition according to the invention can therefore also optionally comprise a $C_3$ to $C_6$ 2-hydroxyalkanoic acid or a $C_3$ to $C_6$-ketoalkanoic acid or a mixture thereof. Examples of such 2-hydroxyalkanoic acids are 2-hydroxypropanoic acid, 2-hydroxybutanoic acid, 2-hydroxy-2-methylpropanoic acid, 2-hydroxypentanoic acid, and 2-hydroxyhexanoic acid. The preferred $C_3$ to $C_6$ 2-hydroxyalkanoic acid is 2-hydroxypropanoic acid. Examples of such 2-ketoalkanoic acids are 2-ketopropanoic acid, 2-ketobutanoic acid, 2-keto-2-methylpropanoic acid, 2-ketopentanoic acid and 2-ketohexanoic acid.

The advantage of employing such $C_3$ to $C_6$ 2-hydroxyalkanoic acids or 2-ketoalkanoic acids is thought to be due to their ability to improve the plasticisation of skin derived from topical application of 2-hydroxyoctanoic acid or 2-ketooctanoic acid. This property can be confirmed by observing the increase in the extensibility of stratum corneum beyond that normally obtainable following the topical application of the substituted octanoic acid without added $C_3$ to $C_6$2-hydroxyalkanoic acid or $C_3$ to $C_6$2-ketoalkanoic acid.

The amount of $C_3$ to $C_6$2-hydroxyalkanoic acid and/or $C_3$ to $C_6$2-ketoalkanoic acid that can be employed in the composition of the invention is from 0.1 to 20%, preferably from 1 to 10% by weight of the composition.

It is apparent that if the composition contains less than 0.1% by weight of at least one of these acids, then the benefit in terms of improved plasticisation of the skin is unlikely to be demonstrated, whereas if the composition contains more than 20% by weight of one of these acids, then it is unlikely that the effectiveness of the composition in further plasticising the skin will be improved.

The composition according to the invention can also optionally contain an alkanol having from 1 to 4 carbon atoms in the molecule, in order to provide a vehicle and solvent for the substituted octanoic acid, and also to enhance the antibacterial properties of the composition. The presence of the alkanol can also enhance the skin degreasing properties of the composition.

Examples of suitable alkanols include methanol, ethanol, propan-1-ol, propan-2-ol, butan-1-ol, butan-2-ol and 2-methylpropan-2-ol. The preferred alkanol is ethanol.

The amount of the $C_1$ to $C_4$ alkanol that can optionally be employed in the composition of the invention is from 1 to 80%, preferably from 2 to 40% by weight of the compos tion.

The composition according to the invention can also optionally contain a humectant to prevent excessive drying out of the skin following topical application of the composition.

Examples of suitable humectants include $C_2$ to $C_4$ alkane diols, such as ethane-1,2-diol and its corresponding dimer and trimer, propane-1,2-diol, butane-1,3-diol, or polymers thereof, such as polyethane diol having molecular weight of up to 10,000, and polypropane diol having a molecular weight of up to 400. Further examples of humectants are "moisturisers" such as sodium pyrrolidone carboxylate, sodium lactate, triethanolamine lactate and sodium chloride.

The amount of humectant such as an alkane diol monomer or the corresponding polymer, when employed, will normally form from 1 to 95%, preferably from 15 to 40% by weight of the composition.

The composition according to the invention can also optionally contain other skin benefit agents which are intended to improve the condition of healthy skin or which are intended to supplement or enhance the effect of the substituted octanoic acid in the treatment or prevention of acne.

Particularly preferred skin benefit agents include wound healing enhancers, such as zinc sulphate; degreasing agents, such as β-cyclodextrin and sodium desoxycholate; anti-inflammatory agents such as allantoin, comedolytic agents such as salicylic acid; and antibiotics such as tetracyclines.

Examples of other active ingredients that can also be employed include sunscreen agents, germicides, deodorants and antiperspirants.

As is stated herein the substituted octanoic acids have the ability to decrease the resistance of skin to deformation by an applied stress, i.e. of increasing plasticisation, and this is determined by measuring the increase in extensibility of stratum corneum.

It has also been discovered that this benefit of increasing the plasticisation of the skin can be further enhanced by including in the composition according to the invention a plasticisation potentiator in addition to the substituted octanoic acid. The plasticisation potentiator will have little or no effect on increasing skin plasticisation when used alone: it is only when combined with the substituted octanoic acid that a substantial increase in skin plasticisation is realised.

While screening many compounds for their ability to potentiate the increase in skin plasticisation following topical application of a substituted octanoic acid, it was observed that they were all compounds which were capable of substantially increasing the critical micelle concentration of nonionic surfactants. Such compounds photodensitometry using a Zeiss spectrophotometer based upon simultaneous reflectance/transmission.

The results which are shown in Table 6 indicated that twice daily topical application of the 2-hydroxyoctanoic acid solution significantly reduced (P<0.01) the free fatty acid:triglyceride ratio of sebum within 7 days.

TABLE 6

Effect of 2-hydroxyoctanoic acid solution upon sebum FFA/TG ratio in vivo

| Days of Treatment | Mean FFA/TG ratio (N = 14) | Mean Reduction (%) |
|---|---|---|
| 0 | 0.64 | — |
| 7 | 0.45* | 30 |
| 14 | 0.42* | 34 |

*Significant difference at p < 0.05.

The 2-hydroxy and 2-keto derivatives of octanoic acid ($C_8$) have been shown to be superior in several respects to the corresponding derivatives of acids of shorter chain length ($C_4$ and $C_6$).

This superiority has been demonstrated in terms of superior extensibility of stratum corneum, which can be equated with general skin benefit, and in terms of superior inhibition of skin microflora and control of skin pH, which can be equated with conditions conducive to the prevention and cure of acne.

(iv) Extensibility of stratum corneum

Extensibility measurements on undamaged and solvent damaged stratum corneum were carried out following treatment with solutions of 2-hydroxy alkanoic acids according to the following method.

Measurement of the extensibility of stratum corneum

Extensibility measurements are carried out using stratum corneum taken from guinea-pig footpads.

Substrate

Guinea-pig footpads are heat separated to produce whole epidermis. Samples are cut with a length of about 20 mm and a width of 2 mm. The extensibility of this whole epidermis may be primarily attributed to the stratum corneum with the underlying tissues having little contribution.

Treatment

The extensibility of each of 6 samples is measured at constant relative humidity, 20° C., after they have been soaked in water for 3 hours at 20° C., blotted dry and equilibrated at constant RH, 20° C. Each sample is soaked in the test solution for 3 hours at 20° C., blotted dry and re-equilibrated at 65% RH, 20° C., then re-measured at this RH.

Instrument

The extensibility is measured by a technique essentially similar to that described by J. D. Middleton in Br. J. Derm. 80, 437. The instrument is a version of the Instron tensile tester and is used to measure the fractional increase in extension of the samples of epidermis for increasing longitudinal stress. The temperature and relative humidity of the environment around the sample under test are carefully controlled and measured ($\pm 1°$ C. and $\pm 1\%$ RH). The samples are stretched at a rate of 1 mm min$^{-1}$. Each sample is stretched up to the limit of its "Hookean" region, returned to its original length, and re-stretched a further 3 times with interim recovery periods. Mean values of % extension per 100 g load (taken from the linear stress vs strain region) are calculated from the last three extensions. Results are described as the mean ratio of extensibility after soaking in test solution to extensibility after soaking in water.

In one particular experiment, the solutions employed were 0.15M aqueous solutions of the 2-hydroxy acids at a pH value of from 2 to 3. A neutralising agent to adjust the pH value to from 3 to 5 was not employed so that the influence in each case of the free acid could be evaluated. The results obtained showed that treatment with 2-hydroxyoctanoic acid induced a significant increase in extensibility as compared with the corresponding $C_3$, $C_4$, $C_6$ and $C_{10}$ hydroxy acids. These results are summarised in Table 7 below.

TABLE 7

Extensibility ratios of solvent damaged guinea-pig footpads before and after treatment with various 2-hydroxyalkanoic acid

| 0.15 M aqueous solution of acid | pH | Extensibility ratio treated/untreated (mean of 20 samples) |
|---|---|---|
| Lactic acid ($C_3$) | 2.35 | 1.3 |
| 2-hydroxy-n-butyric ($C_4$) | 2.20 | 1.3 |
| 2-hydroxy-iso-butyric ($C_4$) | 2.30 | 2.0* |
| 2-hydroxyhexanoic ($C_6$) | 2.40 | 2.5* |
| 2-hydroxyoctanoic ($C_8$) | 2.40 | 5.1* |
| 2-hydroxydecanoic ($C_{10}$) | 3.19 | 2.4* |

*Significant at P 0.02 level by T-test.
Extensibility measurements made a constant RH of 81%.

Unbuffered saturated solutions of 2-hydroxy lauric acid ($C_{12}$) and of 2-hydroxy myristic acid ($C_{14}$), both of which had a pH of 7, were also tested in the same way using guinea pig stratum corneum: there was however no significant difference in extensibility demonstrated between untreated and treated footpads for each of these acids probably because of their low solubility in water.

Otherwise, the tabulated results show a superiority for 2-hydroxy octanoic acid ($C_8$) as compared with an insignificant effect after treatment with both lactic acid ($C_3$) and 2-hydroxy-n-butyric acid ($C_4$), and a relatively poor response after treatment with 2-hydroxyisobutyric acid ($C_4$), and a reduced effectiveness with 2-hydroxyhexanoic acid ($C_6$).

Evidence for the choice of a preferred skin pH of 4.0 when the composition is intended for the treatment of acne The ability of bacteria to survive on the skin surface was studied at a range of pH values of from pH 4 to 7.

A series of solutions of 2-hydroxyoctanoic acid each adjusted with triethanolamine to a pH value within the range of pH 4.0 to 7.0 were accordingly applied to the skin twice daily for seven days, and the reduction in anaerobic bacterial count measured at the end of this treatment.

The results of this experiment are shown in Table 8, from which it will be noted that the reduction in bacterial count was substantial at pH 4.0, whereas the reduction in bacterial count fell off rapidly at skin pH values of 4.5 and above.

These compositions can be applied to the skin using any of the devices referred to hereinbefore or can be administered by the hand or by finger application. Excellent results in the treatment of acne can be obtained by topical application of these compositions once or several times daily to the affected area of skin.

Evidence for the choice of the substituted octanoic acid (i) Effect on skin pH

An in vivo comparison of the influence separately of the cosmetically acceptable hydroxy acids, lactic acid, 2-hydroxyhexanoic acid and 2-hydroxyoctanoic acid on skin pH has been made, it being appreciated that the acid which maintains the pH of the skin at a low level for the longest time would be the most effective in inhibiting skin microflora. Hydroxy alkanoic acids of chain length longer than 8 carbon atoms were not tested in this way in view of their tendency to cause skin irritation.

In each case, the acids were adjusted to pH 4 with triethanolamine.

The results of this comparison are shown in Table 3 from which it will be noted that each of the three acids effected a drop in skin pH from about 5.5 to about 4 within 1 minute of application. The solution containing 2-hydroxyoctanoic acid maintained the pH of the skin at or near pH 4 for at least 7 hours, whereas that containing lactic acid was effective in this respect for less than 1 hour. The solution containing 2-hydroxyhexanoic acid was capable of maintaining the pH of the skin at or near pH 4 for only 1 hour before the pH began to revert to its natural value of about pH 5.5. These results clearly indicate that the solution of 2-hydroxyoctanoic acid shows a remarkable and unexpected ability to maintain the pH of the skin at or about pH 4 for a longer period than expected.

TABLE 3

EFFECT OF 2-HYDROXY ACIDS UPON SKIN SURFACE pH

| Time following application of 2-hydroxy acid | Skin surface pH value | | |
|---|---|---|---|
| | $2\text{-}OHC_3$ acid | $2\text{-}OHC_6$ acid | $2\text{-}OHC_8$ acid |
| Zero | 5.5 | 5.5 | 5.5 |
| 1 minute | 4.4 | 4.2 | 4.0 |
| 1 hour | 4.7 | 4.4 | 4.0 |
| 2 hours | 5.3 | 4.6 | 4.0 |
| 3 hours | 5.5 | 4.8 | 4.2 |
| 4 hours | 5.5 | 5.0 | 4.3 |
| 5 hours | 5.5 | 5.3 | 4.4 |
| 6 hours | 5.5 | 5.4 | 4.4 |
| 7 hours | 5.5 | 5.5 | 4.4 |

(ii) Effect on skin microflora

An in vivo comparison of the influence separately of lactic acid, 2-hydroxyhexanoic acid and 2-hydroxyoctanoic acid on skin microflora has also been made, it being appreciated that the acid which effected the greatest reduction in bacterial count at the skin surface would be the most effective in reducing the accumulation of free fatty acids, resulting from bacterial lipase activity, which are implicated in the development of the acne comedone.

In each case, the acids were adjusted at pH 4 with triethanolamine, and counts of both aerobic and anaerobic bacteria were made by scrubbing the skin after twice daily applications of each acid at intervals up to 14 days.

The results of this comparison are shown in Tables 4 and 5 from which it will be noted that 2-hydroxyoctanoic acid was more effective in reducing both the aerobic count and the anaerobic count, than either lactic acid or 2-hydroxyhexanoic acid.

TABLE 4

EFFECT OF 2-HYDROXY ACIDS UPON RECOVERABLE SKIN SURFACE AEROBES IN-VIVO

| Test solutions: 150 mM 2-hydroxy acid, in water, pH 4.0 with TEA - twice daily application | No. of subjects | Mean log count | | |
|---|---|---|---|---|
| | | Day: 0 | 7 | 14 |
| Lactic acid | 8 | 4.9438 | 5.0268 | 5.1368 |
| 2-hydroxy hexanoic acid | 8 | 5.2836 | 4.5568* (14%) | 4.1212* (22%) |
| 2-hydroxy octanoic acid | 8 | 4.9480 | 3.2425* (34%) | 3.3955* (31%) |
| Control (distilled water) | 8 | 4.9438 | 5.0663 | 4.9955 |

*Significant at the $p<0.05$ level by paired t-test.
(%)represents mean % reduction in the log number, relative to day 0.

TABLE 5

Effect of 2-hydroxy acids upon recoverable skin surface anaerobes in vivo

| Test solutions: 150 mM 2-hydroxy acid, in water, pH 4.0 with TEA - twice daily application | No. of subjects | Mean log count | | |
|---|---|---|---|---|
| | | Day: 0 | 7 | 14 |
| Lactic acid | 8 | 6.9328 | 7.2681 | 6.8000 (2%) |
| 2-hydroxy hexanoic acid | 8 | 6.8125 | 6.6400 (3%) | 6.2000 (9%) |
| 2-hydroxy octanoic acid | 8 | 6.8 | 5.447* (20%) | 5.7905* (15%) |
| Control (distilled water) | 8 | 6.8125 | 6.81 | 7.2603 |

*Significant at the $p<0.05$ level by paired t-test.
(%)represents mean % reduction in the log number, relative to day 0.

It was concluded that the maintenance of a low skin pH for a relatively long time together with a substantial reduction in bacterial count provided irrefutable evidence of the effectiveness of 2-hydroxyoctanoic acid in establishing conditions at the skin surface conducive to the regression of acne.

In similar tests, in which octanoic acid was compared with 2-hydroxyoctanoic acid, it was shown that omission of the hydroxyl group from the 2 position resulted in a marked reduction in antibacterial activity and in the inability to maintain the skin pH at or about 4 for more than a very short time. It was concluded therefore that unsubstituted octanoic acid would not be suitable for treating acne.

(iii) Effect on accumulation of free fatty acids

The ability of 2-hydroxyoctanoic acid to reduce the accumulation in sebum of free fatty acids was determined following topical application of this acid twice daily over a 14 day period. The fall in sebum free fatty acids was expressed in terms of the free fatty acid:triglyceride ratio and was made by extracting sebum with chloroform:methanol 2:1 one hour after treatment with a 2.4% solution of 2-hydroxyoctanoic acid. The extracts were analysed by thin layer chromatography using G plates. The initial solvent system employed was diethyl ether, hexane, acetic acid (30:70:1, by volume); after this had travelled halfway up each plate, the solvent system was changed to diethyl ether, hexane, acetic acid (10:90:1, by volume), and re-run. The plates were then charred using 50% sulphuric acid in aqueous ethanol at 180° C. for 15 minutes. The plates were analysed by

TABLE 8

EFFECT OF pH OF 2-HYDROXYOCTANOIC ACID SOLUTION UPON RECOVERABLE SKIN SURFACE ANAEROBES IN-VIVO

Test solutions:
2-OH—$C_8$
(150 mM) solutions in water, varying pH, neutralised with TEA - twice daily application

| pH | No. of subjects | Day: 0 | Mean log count 7 |
|---|---|---|---|
| pH 4.0 | 8 | 6.8 | 5.447* (20%) |
| pH 4.5 | 8 | 6.9368 | 6.59 (5%) |
| pH 5.5 | 8 | 7.1382 | 7.09 (1%) |
| pH 7.0 | 8 | 6.7828 | 6.5793 (3%) |

*Significant at the p<0.05 level by paired t-test.
(%)represents mean % reduction in the log number, relative to day 0.

It was concluded that the range of pH values within which the composition of the invention was most effective, discounting very low pH values which might give rise to skin irritation, was within a very narrow band around pH 4, i.e. from pH 3.8 to 4.5, although values slightly outside this range, namely from pH 3 to pH 5 are effective.

Evidence for the superiority of 2-hydroxyoctanoic acid, ethyl lactate mixture

(i) Effect on skin microflora

An in vivo comparison of the influence of (i) 2-hydroxyoctanoic acid, (ii) ethyl lactate, and (iii) a mixture of 2-hydroxyoctanoic acid and ethyl lactate on skin microflora has been made.

In each case lotions containing the acid, the ester or the mixture of acid and ester were buffered to pH 4, and counts of both aerobic and anaerobic bacteria were made by swabbing the skin after twice daily applications of each lotion at intervals up to 14 days.

The results of this comparison are shown in Tables 9 and 10, from which it will be noted that the lotion containing both 2-hydroxyactanoic acid and ethyl lactate was surprisingly superior in reducing bacterial counts at the skin surface, compared with the effect noted with either the 2-hydroxyoctanoic acid or ethyl lactate when used separately.

TABLE 9

A comparison of the effect of (i) 2-hydroxyoctanoic acid, (ii) ethyl lactate and (iii) a mixture of 2-hydroxyoctanoic acid and ethyl lactate upon recoverable skin surface aerobes in-vivo

| Lotions | No. of subjects | Day: 0 | Mean log count 7 | 14 |
|---|---|---|---|---|
| (i) 2-hydroxyoctanoic acid | 8 | 5.28 | 3.54* (33%) | 3.36 (36%) |
| (ii) Ethyl lactate | 8 | 5.06 | 4.00* (21%) | 3.54* (30%) |
| (iii) 2-hydroxyoctanoic acid plus ethyl lactate | 8 | 5.30 | 2.80* (47%) | 3.12* (41%) |

Notes:
*Significant at the p <0.05 level by paired t-test.
(%) represents mean % reduction in the log number, relative to day 0.
Lotion formulations (% by weight)
(i) 75 mM 2-hydroxyoctanoic acid + 45% ethanol + 20% butylene glycol + water to 100%; pH adjusted to 4.0 with triethanolamine.
(ii) 11.5% ethyl lactate + 20% butylene glycol + 45% ethanol + water to 100%, pH adjusted to 4.0 with triethanolamine.
(iii) 75 mM 2-hydroxyoctanoic acid + 11.5% ethyl lactate + 45% ethanol + 20% butylene glycol + water to 100%; pH adjusted to 4.0 with triethanolamine.

TABLE 10

A comparison of effect of (i) 2-hydroxyoctanoic acid, (ii) ethyl lactate and (iii) a mixture of 2-hydroxyoctanoic acid and ethyl lactate upon recoverable skin sufrace anaerobes in-vivo

| Lotions | No. of subjects | Day: 0 | Mean log count 7 | 14 |
|---|---|---|---|---|
| (i) 2-hydroxyoctanoic acid | 23 | 6.64 | 4.74* (29%) | 4.23* (36%) |
| (ii) Ethyl lactate | 23 | 6.81 | 5.65* (17%) | 4.56* (33%) |
| (iii) 2-hydroxyoctanoic acid plus ethyl lactate | 23 | 6.70 | 3.41* (49%) | 3.61* (46%) |

Notes:
*Significant at the p<0.05 level by paired t-test.
(%)represents mean % reduction in the log number, relative to day 0.
Lotion formulations (% by weight)
(i) 75 mM 2-hydroxyoctanoic acid + 45% ethanol + 20% butylene glycol + water to 100%; pH adjusted to 4.0 with triethanolamine.
(ii) 11.5% ethyl lactate + 20% butylene glycol + 45% ethanol + water to 100%, pH adjusted to 4.0 with triethanolamine.
(iii) 75 mM 2-hydroxyoctanoic acid + 11.5% ethyl lactate + 45% ethanol + 20% butylene glycol + water to 100%; pH adjusted to 4.0 with triethanolamine.

(ii) Effect on extensibility of stratum corneum

Extensibility measurements on stratum corneum were carried out following treatment with creams containing 2-hydroxyoctanoic acid alone or when mixed with ethyl lactate and/or 2-hydroxypropionic acid according to the method described earlier in this specification. The results obtained are summarised in Table 11 below.

TABLE 11

Extensibility ratios of guinea-pig footpad stratum corneum before and after treatment with creams containing 2-hydroxyoctanoic acid with and without ethyl lactate and/or 2-hydroxypropionic acid

| Cream ingredients | % by weight | Extensibility ratio treated/untreated (mean of 20 samples) |
|---|---|---|
| (i) 2-hydroxyoctanoic acid | 3.2 | 2.0 |
| (ii) 2-hydroxyoctanoic acid + ethyl lactate | 2.0 / 7.5 | 3.0 |
| (iii) 2-hydroxyoctanoic acid + 2-hydroxypropionic acid | 2.0 / 5.0 | 9.1 |
| (iv) 2-hydroxyoctanoic acid + 2-hydroxypropionic acid + ethyl lactate | 2.0 / 5.0 / 7.5 | 12.2 |

In each case the pH value of the cream was adjusted to from 3.8 to 4.0, and extensibility measurements were made a constant RH of 65%.

These results confirm that the substantial increase in the extensibility of stratum corneum of about two fold following treatment with 2-hydroxyoctanoic acid alone can be increased dramatically by up to 6 fold by incorporating ethyl lactate and 2-hydroxypropionic acid in the treatment cream, while neither of these substances materially increases stratum corneum extensibility when used alone under similar treatment conditions.

These results suggest that compositions for topical application to human skin containing 2-hydroxyoctanoic acid and either or both ethyl lactate and 2-hydroxypropionic acid would be highly effective in softening the skin and making it more supple and flexible.

The invention is illustrated by the following examples.

EXAMPLES 1-4

The following formulations represent lotions which can be used in the treatment or prevention of acne according to the invention.

|  | % w/w | | | |
| --- | --- | --- | --- | --- |
|  | 1 | 2 | 3 | 4 |
| Sterilised demineralised water | 34 | 32 | 30 | 23 |
| Hydroxyethyl cellulose | 0.4 | — | 0.4 | — |
| Absolute ethanol | 25 | 25 | 25 | 25 |
| Propane-1,2-diol* | — | — | 38.4 | 38.4 |
| Butane-1,3-diol* | 38.4 | 38.8 | — | — |
| Para methyl benzoate | 0.2 | 0.2 | 0.2 | 0.2 |
| 2-hydroxyoctanoic acid | 1 | — | 5 | 1.2 |
| 2-ketooctanoic acid | — | 3 | — | 1.2 |
| Perfume | 1 | 1 | 1 | 1 |
|  | 100 | 100 | 100 | 100 |
| pH adjusted with triethanolamine to | 4.1 | 3.9 | 4.0 | 4.2 |

*plasticisation potentiators

EXAMPLES 5-8

The following formulations represent lotions which can be used in the treatment or prevention of acne according to the invention.

|  | % w/w | | | |
| --- | --- | --- | --- | --- |
|  | 5 | 6 | 7 | 8 |
| Water | 58 | 56 | 29 | 27 |
| Ethanol | 10 | 10 | 10 | 10 |
| Propane-1,2-diol* | 30 | 0 | 55 | 0 |
| Butane-1,3-diol* | 0 | 30 | 0 | 55 |
| 2-hydroxyoctanoic acid | 2 | — | 6 | 2 |
| 2-ketooctanoic acid | — | 2 | — | 2 |
|  | 100 | 100 | 100 | 100 |
| pH adjusted with triethanolamine to | 4 | 3.8 | 4.4 | 4.3 |

*plasticisation potentiators

EXAMPLES 9-12

The following formulations represent creams which can be used in the treatment or prevention of acne according to the invention.

|  | % w/w | | | |
| --- | --- | --- | --- | --- |
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| 2-hydroxyoctanoic acid | 2.4 | — | 2.4 | — |
| 2-ketooctanoic acid | — | 2.4 | — | 2.4 |
| Triethanolamine | 0.75 | 0.75 | 0.75 | 0.75 |
| Butane-1,3-diol* | 3 | 3 | 3 | 3 |
| Xanthan gum | 0.3 | 0.3 | 0.3 | 0.3 |
| Preservative | 0.4 | 0.4 | 0.4 | 0.4 |
| Water | 81.15 | 81.15 | 81.15 | 81.15 |
|  | 100 | 100 | 100 | 100 |
| pH adjusted with triethanolamine to | 4.0 | 4.0 | 4.0 | 4.0 |

*plasticisation potentiator

EXAMPLE 13

The following formulation represents a lotion which can be used in the treatment or prevention of acne according to the invention.

|  | % w/w |
| --- | --- |
| Butane-1,3-diol* | 20 |
| Ethanol* | 45 |
| 2-hydroxyoctanoic acid | 1.2 |
| Triethanolamine to pH 4 about | 1 |
| Water to | 100 |

*plasticisation potentiators

EXAMPLE 14

This example illustrates a water-in-oil high internal phase emulsion containing 2-hydroxyoctanoic acid according to the invention.

The emulsion consisted of 10% by volume oily phase and 90% by weight aqueous phase.

The oily phase and the aqueous phase had the following constitution:

|  | % w/w |
| --- | --- |
| Oily phase | |
| Sorbitan monooleate | 20 |
| Quarternium-18 hectorite | 5 |
| Liquid paraffin | 75 |
| Aqueous phase | |
| 2-hydroxyoctanoic acid | 2.4 |
| Xanthan gum | 1 |
| Sodium chloride (1% w/w solution) | 96.3 |
| Preservative | 0.3 | pH adjusted to pH 5 with triethanolamine.

The emulsion was prepared by taking 10 parts by volume of the oily phase and to it adding slowly with stirring 90 parts by volume of the aqueous phase.

The high internal phase water-in-oil emulsion so formed can be applied topically to improve skin condition generally or to alleviate a dry, scaly condition and in the treatment of acne.

EXAMPLE 15

This example illustrates a water-in-oil high internal phase emulsion containing 2-ketooctanoic acid according to the invention.

The emulsion consisted of 10% by volume oily phase and 90% by weight aqueous phase.

The oily phase and the aqueous phase had the following constitution:

|  | % w/w |
| --- | --- |
| Oily phase | |
| Castor oil polyglyceryl ester | 20 |
| Hydrophobic silica | 5 |
| Sunflower seed oil | 75 |
| Aqueous phase | |
| 2-ketooctanoic acid | 2.4 |
| Xanthan gum | 1 |
| Sodium chloride (1% w/w solution) | 96.3 |
| Preservative | 0.3 | pH adjusted to pH 4.5 with triethanolamine.

The emulsion was prepared by taking 10 parts by volume of the oily phase and to it adding slowly with stirring 90 parts by volume of the aqueous phase.

The high internal phase water-in-oil emulsion so formed can be applied topically to improve skin condition generally or to alleviate a dry, scaly condition and in the treatment of acne.

The following examples illustrate 16 to 19 compositions according to the invention which incorporate a plasticisation potentiator (indicated by *).

EXAMPLE 16

A solution contains 3.2% by weight 2-hydroxyoctanoic acid or 2-ketooctanoic acid and 5% by weight of n-methyl-2-pyrrolidone* and is buffered to pH 4 with triethanolamine.

EXAMPLE 17

A creamy oil-in-water emulsion contains 3.2% by weight 2-hydroxyoctanoic acid or 2-ketooctanoic acid, 30% by weight of an oil, an emulsifier having an HLB value of 9 and 5% by weight of 2-pyrrolidone* and is buffered to pH 4 with triethanolamine and emulsifier.

EXAMPLE 18

A gel contains 3.2% by weight 2-hydroxyoctanoic acid or 2-ketooctanoic acid, 5% by weight of butane-1,3 diol*, 1% by weight xanthan gum, and 1% by weight sodium chloride and is buffered to pH 4.5 with triethanolamine.

EXAMPLE 19

A high internal phase water-in-oil emulsion contains 3.2% by weight 2-hydroxyoctanoic acid or 2-ketooctanoic acid, 10% by weight of a branched chain oil, an emulsifier having an HLB of 6 and 5% by weight of propane-1,2-diol* is buffered to pH 4.5 with triethanolamine.

EXAMPLES 20 to 23

The following formulations represent lotions which can be used in the treatment or prevention of acne according to the invention.

|  | % w/w | | | |
| --- | --- | --- | --- | --- |
|  | 20 | 21 | 22 | 23 |
| Sterilised demineralised water | 29 | 27 | 25 | 21 |
| Hydroxyethyl cellulose | 0.4 | — | 0.4 | — |
| Absolute ethanol | 20 | 15 | 25 | 21 |
| Propane-1,2-diol* | — | — | 38.4 | 38.4 |
| Butane-1,3-diol* | 38.4 | 38.8 | — | — |
| Para methyl benzoate | 0.2 | 0.2 | 0.2 | 0.2 |
| 2-hydroxyoctanoic acid | 1 | — | 5 | 5.2 |
| 2-ketooctanoic acid | — | 3 | — | 5.2 |
| Ethyl lactate | 10 | 15 | 5 | 8 |
| Perfume | 1 | 1 | 1 | 1 |
|  | 100 | 100 | 100 | 100 |
| pH adjusted with triethanolamine to | 4.1 | 3.9 | 4.0 | 4.2 |

*plasticisation potentiator

EXAMPLES 24 to 27

The following formulations represent lotions which can be used in the treatment or prevention of acne according to the invention.

|  | % w/w | | | |
| --- | --- | --- | --- | --- |
|  | 24 | 25 | 26 | 27 |
| Water | 52 | 47 | 20 | 18 |
| Ethanol | 10 | 10 | 8 | 5 |
| Propane-1,2-diol* | 30 | 0 | 55 | 0 |
| Butane-1,3-diol* | 0 | 30 | 0 | 55 |
| Ethyl lactate | 6 | 9 | 11 | 14 |
| 2-hydroxyoctanoic acid | 2 | — | 6 | 4 |
| 2-ketooctanoic acid | — | 4 | — | 4 |
|  | 100 | 100 | 100 | 100 |
| pH adjusted with triethanolamine to | 4 | 3.8 | 4.4 | 4.3 |

*plasticisation potentiator

EXAMPLE 28

The following formulation represents a oil-in-water emulsion (a cream) which can be employed topically in the treatment of acne, according to the invention.

|  | % w/w |
| --- | --- |
| 2-hydroxyoctanoic acid | 2.0 |
| 2-hydroxypropionic acid | 5.0 |
| mineral oil | 5.0 |
| thickener | 0.5 |
| emulsifier (EMULSENE 1219+) | 7.0 |
| butane-1,3-diol* | 13.5 |
| preservative | 0.3 |
| water to | 100 | pH adjusted to 4.0 with triethanolamine.
+EMULSEEN is a mixture of cetyl alcohol and polyoxyethylene cetyl ether.
*plasticisation potentiator.

EXAMPLE 29

This example illustrate an oil-in-water cream containing ethyl lactate and a plasticisation potentiator in addition to 2-hydroxyoctanoic acid.

|  | % w/w |
| --- | --- |
| 2-hydroxyoctanoic acid | 2 |
| Mineral oil | 5 |
| Thickener | 0.5 |
| EMULSENE | 7 |
| Butane-1,3-diol* | 13.5 |
| Preservative | 0.3 |
| Ethyl lactate | 7.5 |
| Water to | 100 |

The pH was adjusted to a value of 3.8 with triethanolamine.
*plasticisation potentiator.

EXAMPLE 30

This example illustrates an oil-in-water cream containing both ethyl lactate and 2-hydroxypropionic acid and a plasticisation potentiator in addition to 2-hydroxyoctanoic acid.

|  | % w/w |
| --- | --- |
| 2-hydroxyoctanoic acid | 2 |
| Mineral oil | 5 |
| Thickener | 0.5 |
| EMULSENE | 7 |
| Butane-1,3-diol* | 13.5 |
| Preservative | 0.3 |
| Ethyl lactate | 7.5 |
| 2-hydroxypropionic acid | 5.0 |
| Water to | 100 |

The pH was adjusted to a value of 3.8 with triethanolamine.
*plasticisation potentiator.

What is claimed is:

1. A cosmetically acceptable aqueous composition for topical application to human skin, which comprises:
    (i) from 0.1 to 20% by weight of 2-hydroxyoctanoic acid;
    (ii) from 0.1 to 20% by weight of 2-hydroxypropionic acid; and
    (iii) an amount of an alkanolamine sufficient to adjust the pH of the composition to a value of from 3.8 to 4.5.

* * * * *